US006475115B1

(12) United States Patent
Candito et al.

(10) Patent No.: US 6,475,115 B1
(45) Date of Patent: Nov. 5, 2002

(54) COMPUTER EXERCISE SYSTEM

(76) Inventors: Thomas Candito, 106 Stonecutter Rd., Levittown, NY (US) 11756; Konan Yao, 164-10, 84th Ave. #2C, Jamaica, NY (US) 11432

( * ) Notice: Subject to any disclaimer, the term of this patent is extended or adjusted under 35 U.S.C. 154(b) by 0 days.

(21) Appl. No.: 09/697,834

(22) Filed: Oct. 27, 2000

(51) Int. Cl.$^7$ ................................................ A63B 21/00
(52) U.S. Cl. ................ 482/4; 482/1; 482/901
(58) Field of Search ........................... 482/1–9, 51, 57, 482/900–902

(56) References Cited

U.S. PATENT DOCUMENTS 6,050,924 A * 4/2000 Shea ........................... 482/57
6,179,746 B1 * 1/2001 Delman ........................ 482/6

* cited by examiner

Primary Examiner—Glenn E. Richman
(74) Attorney, Agent, or Firm—Michael I. Kroll

(57) ABSTRACT

A computer exercise system for requiring a user to exercise prior to being granted access to use a computer. The computer exercise system includes a computer having a processor, an exercise device and a scanner connected between the computer and exercise device. The sensor detects use of the exercise device and, upon detecting such use, transmits a signal to the processor. The processor prevents access to the computer until the signal indicating use of the exercise device is received from the scanner for a predetermined period of time. The computer further includes a monitor connected to the processor for displaying an image indicating a period of time for which the signal must be received by the processor from the scanner in order to be granted access to the computer. The processor includes a memory for storing account information for a plurality of individual users, each individual user being assigned an account and each account being assigned a unique user I.D. and password. A keyboard is provided for entering information to access a desired one of the accounts. Each individual account also includes a predetermined exercise time during which a respective user must exercise prior to being granted access to the computer. The sensor may transmit the signal to the processor either through a cable wire or wirelessly.

21 Claims, 7 Drawing Sheets

COMPUTER EXERCISE SYSTEM

BACKGROUND OF THE INVENTION

1. Field of the Invention

The invention relates generally to exercising devices and, more specifically, to an exercising device connected to a computer system whereby use of the exercise device for a predetermined time period activates the computer system to allow operation by the user.

2. Description of the Prior Art

Numerous types of exercise devices have been provided in the prior art. For example, U.S. Pat. Nos. 4,354,676; 890,997; 5,921,891; 5,984,839; 6,010,430 and 6,059,692 all are illustrative of such prior art. While these units may be suitable for the particular purpose to which they would not be as suitable for the purposes of the present invention as heretofore described.

U.S. Pat. No. 4,354,676

Inventor: Gideon B. Ariel

Issued: Oct. 19, 1982

An exerciser bar is supported for rotation and acts against an hydraulic cylinder with the angle of the bar and the pressure in the cylinder measured and fed to a micro computer which, using this input data, controls the cylinder pressure in accordance with a selected exercise program, the micro computer also providing outputs to displays so that the person exercising can monitor his progress.

U.S. Pat. No. 5,890,997

Inventor: Eric S. Roth

Issued: Apr. 6, 1999

A computer system and method for the design, execution and tracking of exercise programs including portable microprocessor controlled data controllers to instruct and record the actual computed workout for the user. A data communication link transfers data between the data controllers and a computer hosting application software and database files for the particular user, exercise and exercise regimen to create and display a customizable and comprehensive exercise system designed for the particular user.

U.S. Pat. No. 5,921,891

Inventor: James Neville Browne

Issued: Jul. 13, 1999

An improved user monitor 102 is a component of the illustrated monitoring system. This system includes a master data processor in the form of a computer 101 arranged to store physical parameter data for a plurality of users. Each user is provided with a user monitor 102 which is arranged to monitor at least one physical parameter of the user during exercise and store data relating to the physical parameter. This data can subsequently be transmitted to the master data processor by pulse transmission from the user monitor down a telephone line 103. The master data processor then compares the received data with the stored data for the user in order to enable monitoring of the progress of the user in an exercise regimen which has been preset for him. At the end of each exercise, the exercise monitor screen shows an effort rating of "EFFORT 12". The client can alter the number anywhere from 6 to 20 by using the keypad 14 on the face of the exercise monitor. The number entered relates to the client's perception of the degree of difficulty experienced during the exercise, for example, 9 is very light, 11 is "fairly light", 14 is "somewhat hard", and 15 is "hard". If a certain undesirable pattern of Effort Rating is detected the monitor is programmed to automatically respond to the undesirable pattern and to slowly alter the prescription.

U.S. Pat. No. 5,984,839

Invention: Eric T. Corkum

Issued: Nov. 16, 1999

A computing can be built into a pre-existing exercise machine so that the person using the machine can view the screen on the computer monitor while engaged in aerobic exercise activity. Keyboard mechanisms are secured to hand rails of the machine, whereby the person can operate the keyboards without releasing his grip on the hand rails. The computer monitor is adjustably supported to provide persons of different heights and head positionments a good view of the viewing screen on the monitor.

U.S. Pat. No. 6,010,430

Inventor: Roy J. Mankovitz

Issued: Jan. 4, 2000

Exercise apparatus for attachment to a chair having a center support post. The apparatus has a foot support, wheels mounted on the respective ends of the foot support for rolling on a floor, and a resilient member that resistance as the foot support is moved. One or more sensors are coupled to the wheels for monitoring a user's body functions during exercise. The sensors provide inputs to software in the user's computer that calculate the level of the user's exercise activity as the user is at work on his/her computer. The results are displayed ont the computer's monitor.

U.S. Pat. No. 6,059,692

Inventor: Paul L. Hickman

Issued: May 9, 2000

An exercise system includes a local system having an exercise apparatus and an associated local computer, where the local computer controls and monitors the operation and use, respectively, of the exercise apparatus. The system further includes a remote system having a remote computer, and a transmission medium including a telephone line that couples the local system to the remote system for data communication between the local system and the remote system. The remote system may receive local system data from the local system concerning the use of the exercise apparatus, and the local system may receive remote system data from the remote system concerning the operation of the exercise apparatus. The local computer preferably controls the operation of the exercise apparatus based upon a modifiable script stored in a read/write memory of the local computer, which can be updated by the remote system. A method for controlling an exercise apparatus includes running a modifiable script on a local computer to control the use and to monitor the operation of an exercise apparatus, and communicating with a remote system to provide the remote system with data concerning the use of the exercise apparatus. The script is stored in read/write memory of the local computer and remote system data received from the remote system may include at least a portion of a new script to be stored in the read/write memory of the local computer.

SUMMARY OF THE PRESENT INVENTION

The present invention relates generally to exercising devices and, more specifically, to an exercising device connected to a computer system whereby use of the exercise device for a predetermined time period activates the computer system to allow operation by the user.

A primary object of the present invention is to provide a computer exercise system that will overcome the shortcomings of prior art devices.

Another object of the present invention is to provide a computer exercise system which is able to insure that a user will exercise their body prior to operating a computer.

A further object of the present invention is to provide a computer exercise system which is able to provide a password for each individual user of a computer, requiring the individual user to exercise for a predetermined amount of time after entering the password and prior to operating the computer.

A yet further object of the present invention is to provide a computer exercise system wherein each user is assigned an individual identification screen name and password which must be entered in order to use the computer.

A still further object of the present invention is to provide a computer exercise system including a processor able to prevent users from accessing software therein until a user identification and password are entered and a predetermined amount of exercise is performed.

An even further object of the present invention is to provide a computer exercise system having an exercise device connected to an input port of a computer for transmitting a signal to a processor of the computer while exercise is being performed by a user.

A still further object of the present invention is to provide a computer exercise system wherein the exercise device includes a scanner to determine if the exercise device is being operated.

Another object of the present invention is to provide a computer exercise system including a timer connected to the processor for monitoring a time period during which exercise must be performed by the user.

An even further object of the present invention is to provide a computer exercise system which is able to regulate the amount of time the user spends on the computer after exercising, the amount of computer time being dependent on the amount of time the user exercises.

A still further object of the present invention is to provide a computer exercise system wherein the exercise device is able to monitor the physical conditioning, e.g. heart rate, blood pressure, etc. of the user and transmit such information to the computer for storage therein and comparisons with previous workouts.

Another object of the present invention is to provide a computer exercise system wherein the user is able to utilize the computer to perform numerous functions including calculations, printing, charting, graphing, generating schedules, cross-referencing results of previous workouts.

A still further object of the present invention is to provide a computer exercise system that is simple and easy to use.

A still further object of the present invention is to provide a computer exercise system that is economical in cost to manufacture.

Additional objects of the present invention will appear as the description proceeds.

A computer exercise system for requiring a user to exercise prior to being granted access to use a computer is disclosed by the present invention. The computer exercise system includes a computer having a processor, an exercise device and a scanner connected between the computer and exercise device. The sensor detects use of the exercise device and, upon detecting such use, transmits a signal to the processor. The processor prevents access to the computer until the signal indicating use of the exercise device is received from the scanner for a predetermined period of time. The computer further includes a monitor connected to the processor for displaying an image indicating a period of time for which the signal must be received by the processor from the scanner in order to be granted access to the computer. The processor includes a memory for storing account information for a plurality of individual users, each individual user being assigned an account and each account being assigned a unique user I.D. and password. A keyboard is provided for entering information to access a desired one of the accounts. Each individual account also includes a predetermined exercise time during which a respective user must exercise prior to being granted access to the computer. The sensor may transmit the signal to the processor either through a cable wire or Tirelessly.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjuction with the accompanying drawings, in which like reference characters designate the same or similar parts throughout the several views.

Figure 6:
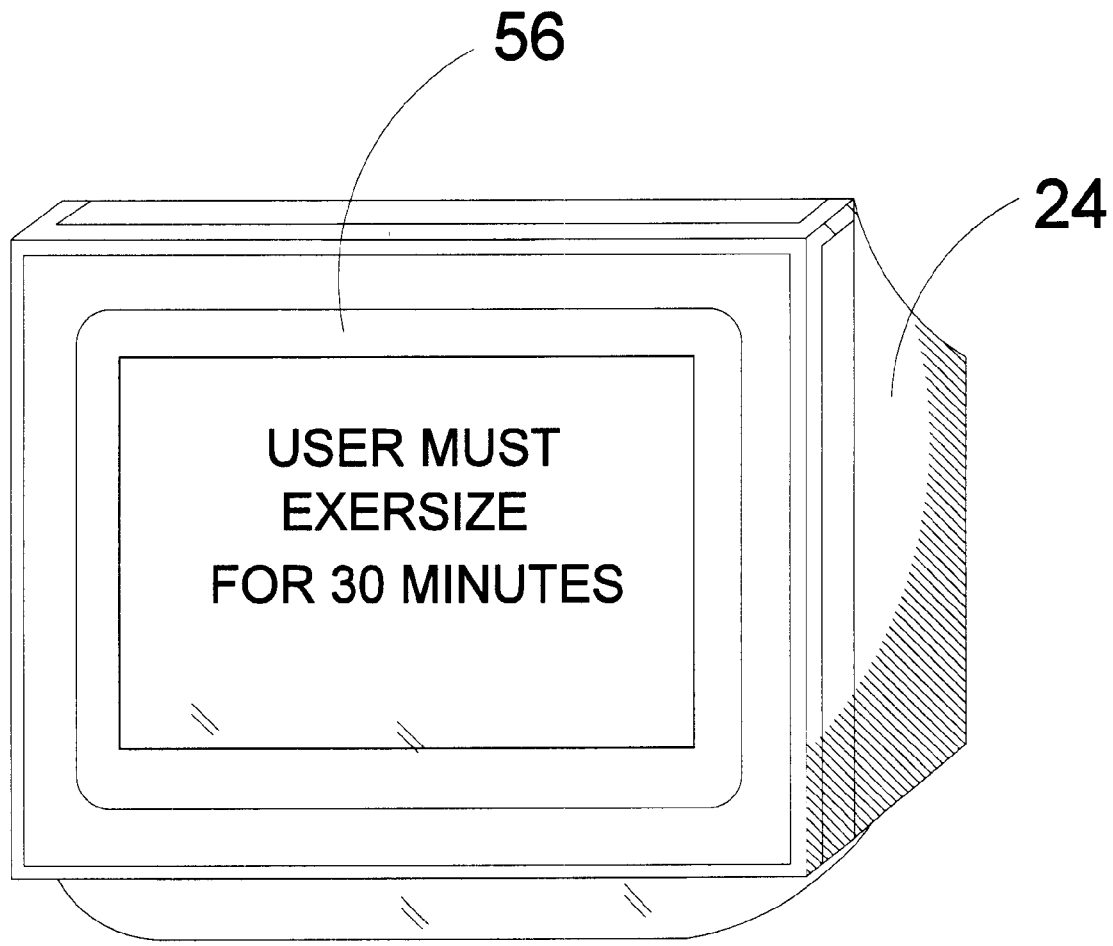
Figure 7:
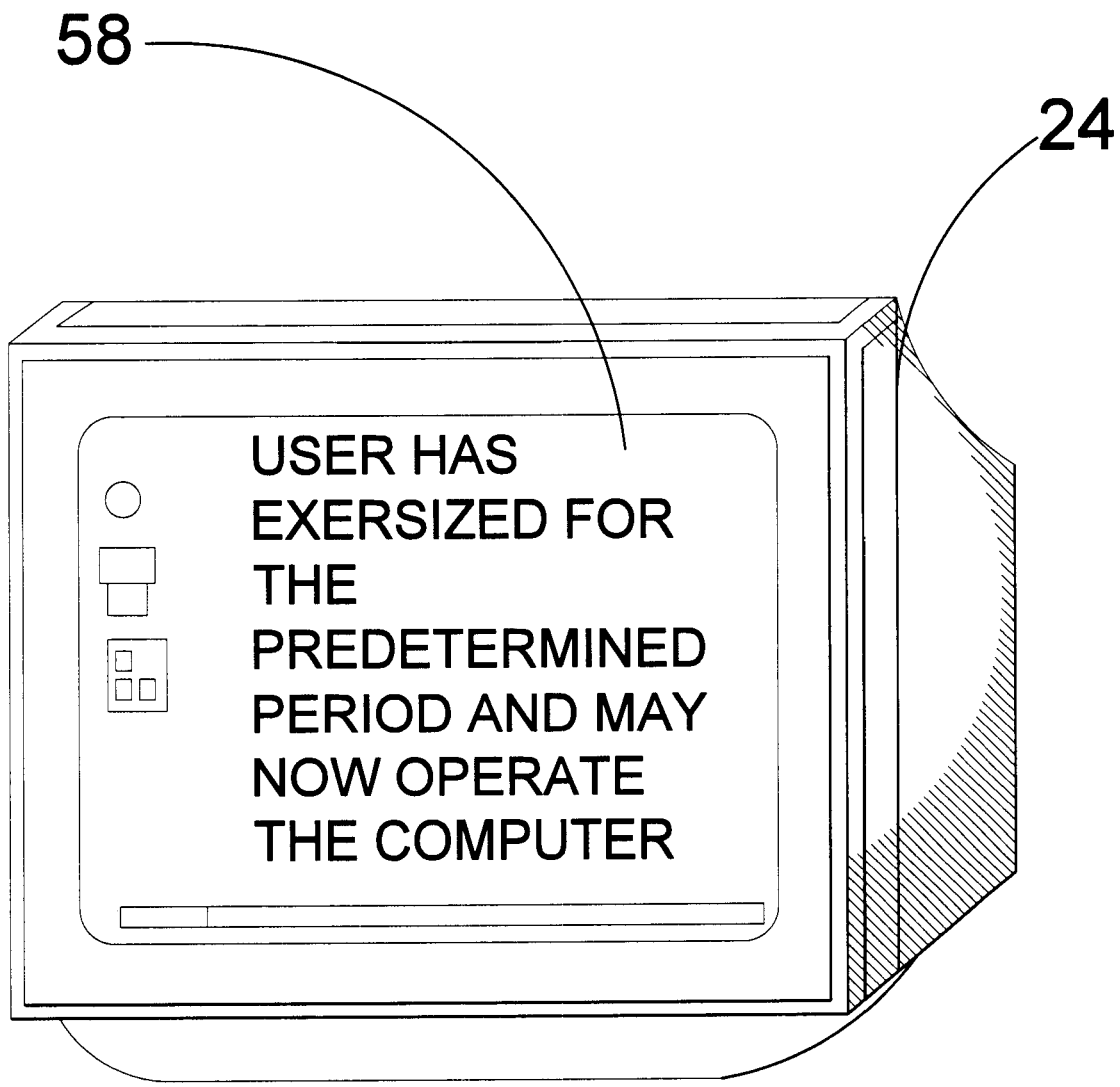

FIG. 6 is a front view of the monitor of the computer exercise system of the present invention showing a display screen displayed after entry of a password indicating the user must exercise for a predetermined amount of time before being able to use the computer; and FIG. 7 is a front view of the monitor of the computer exercise system of the present invention showing a display screen displayed after the user has exercised for a predetermined amount of time indicating the user is now allowed to operate the computer.

DESCRIPTION OF THE REFERENCED NUMERALS

Turning now descriptively to the drawings, in which similar reference characters denote similar elements throughout the several views, the Figures illustrate the computer exercise system of the present invention. With regard to the reference numerals used, the following numbering is used throughout the various drawing figures.

10 computer exercise system of the present invention
12 exercise device
14 computer system
16 processor of computer system
18 keyboard of computer system
20 mouse of computer system
22 mouse pad
24 monitor of computer system
26 CD-ROM drive of computer system
28 floppy diskette drive of computer system
30 power button of computer system
32 cable connecting exercise device to computer system
34 cable connecting mouse to computer system
36 cable connecting keyboard to computer system
38 user
39 display on monitor during use of the exercise machine
40 back side of processor
42 cable connecting monitor to processor
44 power switch for monitor
46 power source
48 sensor
50 timer
52 memory
53 user I.D.
54 log in screen
55 associated password
56 screen displayed after entry of password
58 desktop screen after performing required amount of exercise
60 back side of processor
62 connection port for keyboard
64 connection port for mouse
66 connection port for monitor
68 power cable for processor
70 power cable for monitor
72 input port
74 wireless transmitter
76 receiver
78 physical conditioning monitor

DETAILED DESCRIPTION OF THE PREFERRED EMBODIMENT

Turning now descriptively to the drawings, in which similar reference characters denote similar elements throughout the several views, FIGS. 1 through 7 illustrate the computer exercise system of the present invention indicated generally by the numeral 10.

Figure 1:
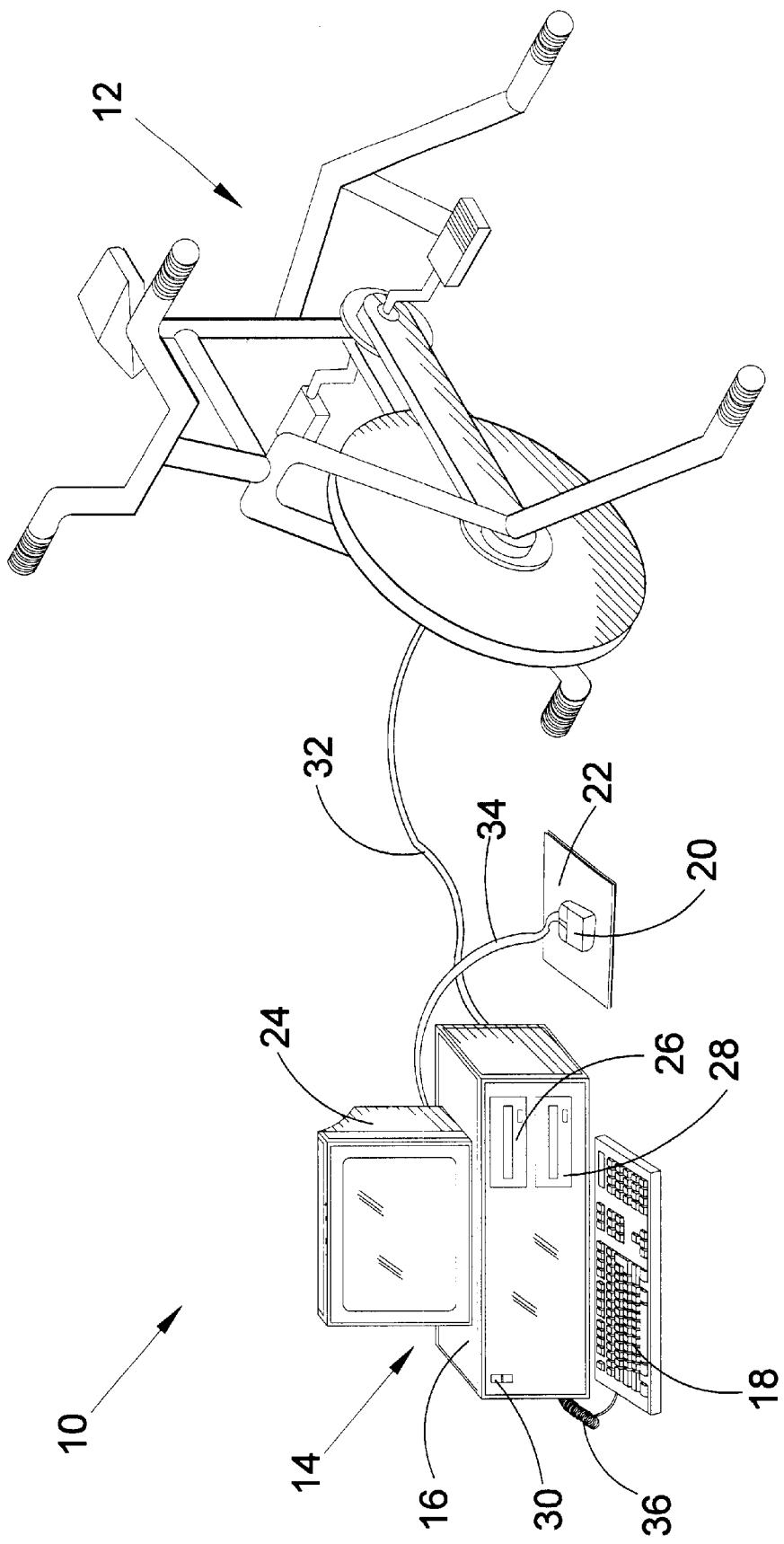
FIG. 1 is a top perspective view of the computer exercise system of the present invention.

The computer exercise system 10 is depicted in FIG. 1 including an exercise device 12 and a computer system 14. The exercise device 12 is depicted as a stationary bicycle. However, any known exercise device may be used in which motion of the exercise device can be monitored to determine that the device is in use. Examples of other such exercise devices which may be used with the computer exercise system of the present invention are treadmills, life cycles, stair climbing machines or any cardiovascular device. These exercise devices may include devices for measuring different physical characteristics of the user such as heartbeat, blood pressure, pulse rate, etc. The computer system 14 is similar to commonly used computer systems.

The computer system 14 includes a processor 16 and a keyboard 18 connected to the processor 16 via a connection wire 36. A mouse 20 is provided as shown positioned on a mouse pad 22. The mouse 20 is connected to the processor 16 via a connection wire 34 and a monitor 24 is connected to the processor 16 for displaying images under the control of the processor 16. The processor 16 is preferably equipped with a CD-ROM drive 26 for receipt of compact discs, a floppy disk drive 28 for receipt of floppy disks and a power switch 30 for turning the computer on and off. The exercise device 12 is connected to an input port of the processor 16 for providing a signal indicating the exercise device 12 is in use to the processor 16. The exercise device 12 is also able to provide signals indicative of the measured physical characteristics of the user to the processor 16 for analysis thereby.

Figure 2:
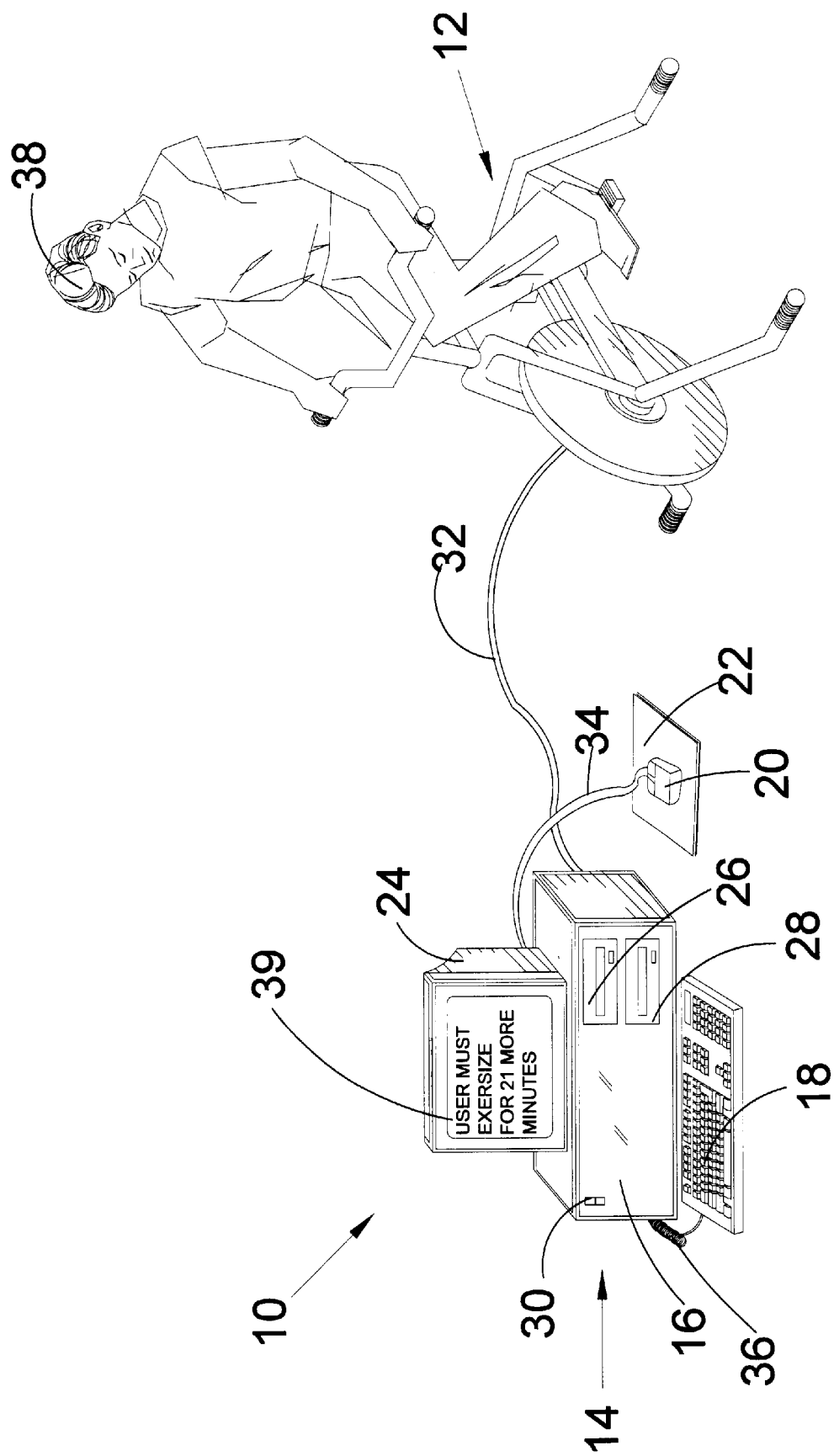
FIG. 2 is a top perspective view of the computer exercise system of the present invention being operated by a user.

FIG. 2 illustrates a user 38 using the exercise device 12 prior to being granted access to the computer 14. As can be seen from this view, the display 39 on the monitor 24 indicates that the user 38 must exercise for a predetermined amount of time prior to being granted access to use the computer 14. The monitor 24 displays the image 39 under the control of the processor 16 for notifying the user of the amount of time the user 38 must continue to exercise before being granted access to use the computer 14. As the user 38 continues to exercise, a signal is transmitted through the connection wire 32 to the processor 16. The processor 16 analyzes this signal and continues to monitor for receipt of this signal for a predetermined amount of time associated with the particular user 38. When the processor 16 determines that the signal has been received for the predetermined amount of time, access to the computer system 14 is granted to the user 38. Should the user not exercise for the predetermined amount of time, the processor 16 will not grant access to the user 38. The processor 16 will continually update the amount of time that the user 38 must continue to exercise by displaying the amount of time remaining on the monitor 24.

Figure 3:
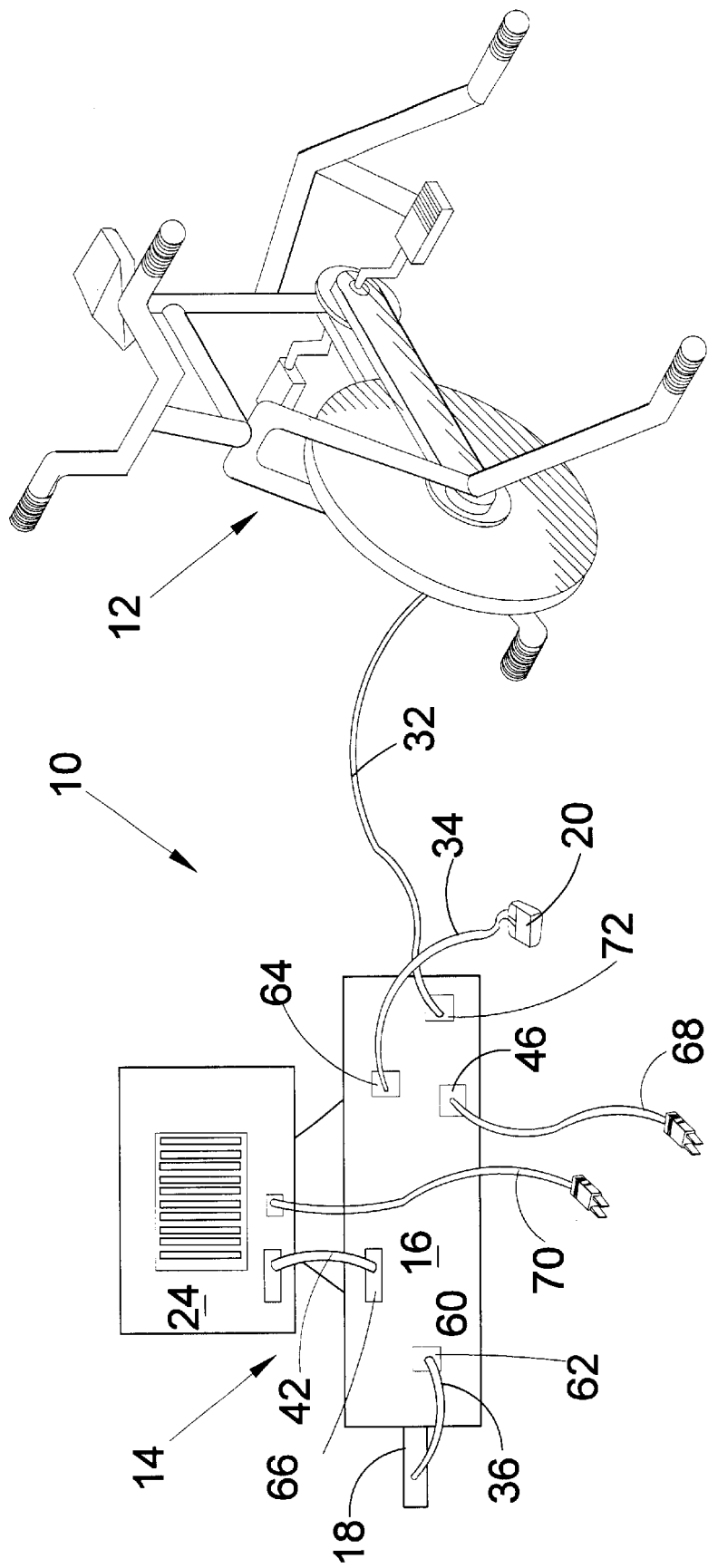
FIG. 3 is back side view of the computer exercise system of the present invention.

A view of the back side 60 of the computer 14 is shown in FIG. 3. As can be seen from this view, the keyboard 18 is connected to a keyboard port 62 on the back side 60 of the processor 16 via the connection wire 36. The mouse 20 is connected to a mouse port 64 on the back side 60 of the processor 16 via the connection wire 34. The monitor 24 is connected to a monitor port 66 on the back side 60 of the processor 16 via the connection wire 42. A power cord 68 extends from the back side 60 of the processor 16 for connection with an external power source. A power cord 70 also extends from a back side of the monitor 24 for connection with an external power source. The exercise device 12 is connected to an input port 72 on the back side 60 of the processor 16 for providing signals from the exercise device 12 indicative of use to the processor 16 for analysis.

Figure 4:
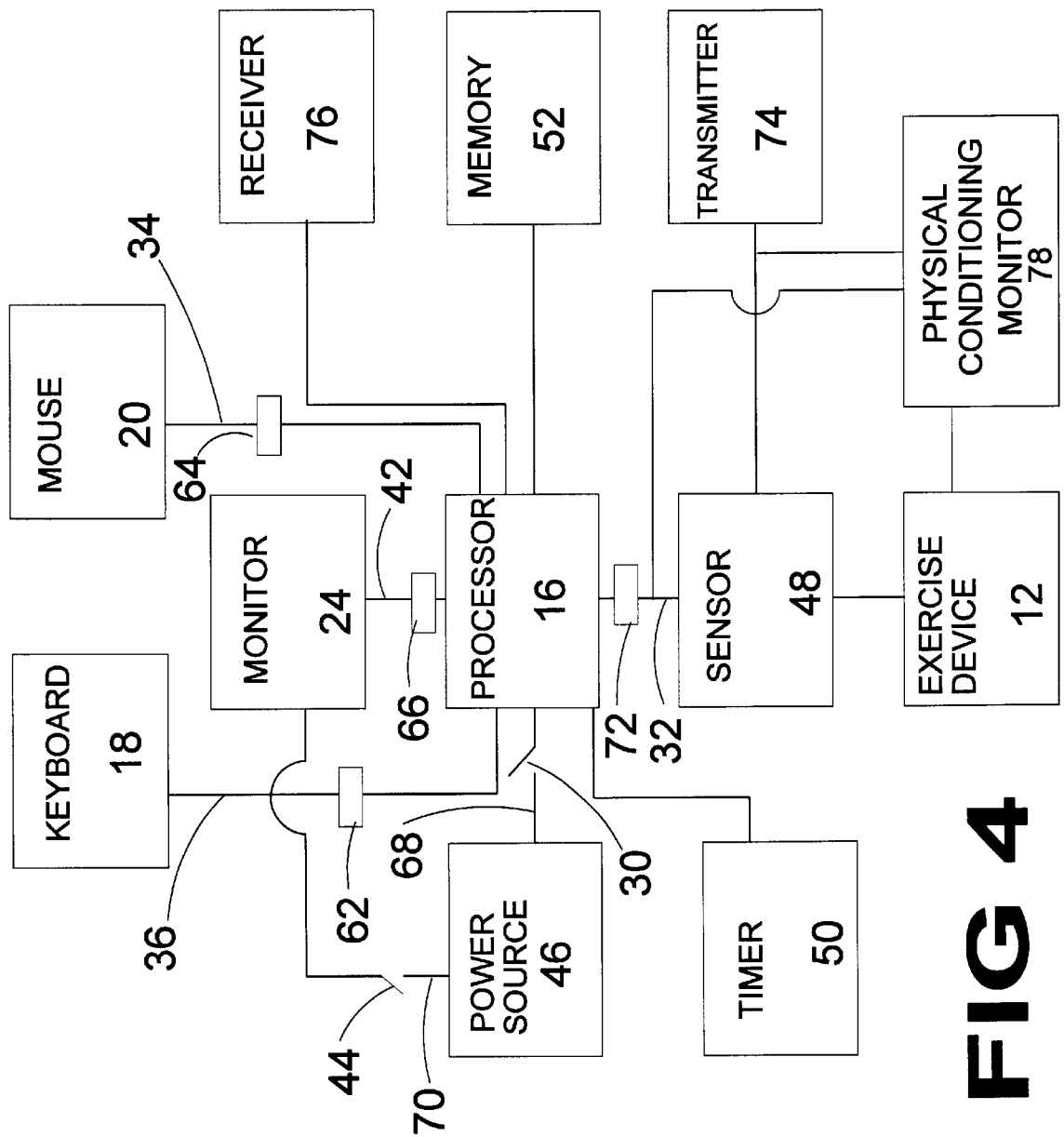
FIG. 4 is a block diagram illustrating the elements of the computer exercise system of the present invention.

A block diagram of the computer exercise system 10 is illustrated in FIG. 4. This figure shows the processor 16 connected to a power source 46 through the power switch 30 and the power cable 68. The processor 16 is also connected to the monitor 24 via the connection port 66 and connection wire 34. The monitor 24 is also connected to the power source 46 via a power switch 44 and the power cable 70. The processor 16 is connected to the keyboard 18 through the keyboard port 62 and the connection wire 36 and to the mouse 20 via the mouse port 64 and connection wire 34. A timer 50 is connected to the processor 16 for counting the time period set for each user 38 to exercise. The timer 50 also monitors a time period during which the user is allowed to use the computer system 14 after exercising. A predetermined time period may be set for each user dependent upon the amount of time spent exercising. A memory unit 52 is connected to the processor 16 for storing all relevant data regarding each potential user of the computer system 14 as well as all other data and programs used by the processor 16 when the computer is being used. The relevant data regarding each user may include a required amount of time for exercise prior to being granted access to the computer system, an amount of time the user is allowed to exercise and physical characteristics of the user measured during exercise. Once the user is granted access to the computer system, the user may perform all sorts of functions including but not limited to calculations, printing, charting, graphing, generating schedules, cross-referencing results of previous workouts.

The exercise device 12 includes a sensor 48 connected thereto for sensing when the exercise device 12 is being used. For example, when the exercise device 12 is a stationary bicycle as shown in FIGS. 1–3, the sensor 48 can be connected to a wheel of the bicycle to sense when the wheel is spinning. Upon detecting that the exercise device 12 is being used, the sensor 48 generates and transmits a signal to the processor 16 via the connection wire 32 and input port 72. Alternatively, the sensor 48 may include a wireless transmitter 74 and the processor may include a receiver 76. When the exercise device 12 is being used, the sensor 48 will transmit a signal through the transmitter 76 indicative of such use. This signal will be received by the receiver 76 and provided to the processor 16 for analysis. The processor 16 activates the timer 50 upon initially receiving the signal from the sensor 48 to begin counting for the predetermined time period. The processor 16 then continues to monitor for receipt of the signal from the sensor 48 for the duration of the predetermined time period. When the timer 50 indicates that the predetermined time period has expired, the processor 16 will grant access to the computer system 14. Should the signal cease to be received from the sensor 48 prior to expiration of the predetermined time period, the processor 16 will not grant access to the computer system 14.

A physical conditioning monitor may also be connected to the exercise device 12 for monitoring physical conditions of the user while exercising. These physical conditions include but are not limited to heart rate, blood pressure and pulse rate. A signal representative of the measured conditions may be transmitted to the processor 16 either through a hardwired connection 32 or by the transmitter 74. The processor 16 is able to store the transmitted signals and analyze the signals to determine the physical condition of the user.

Figure 5:
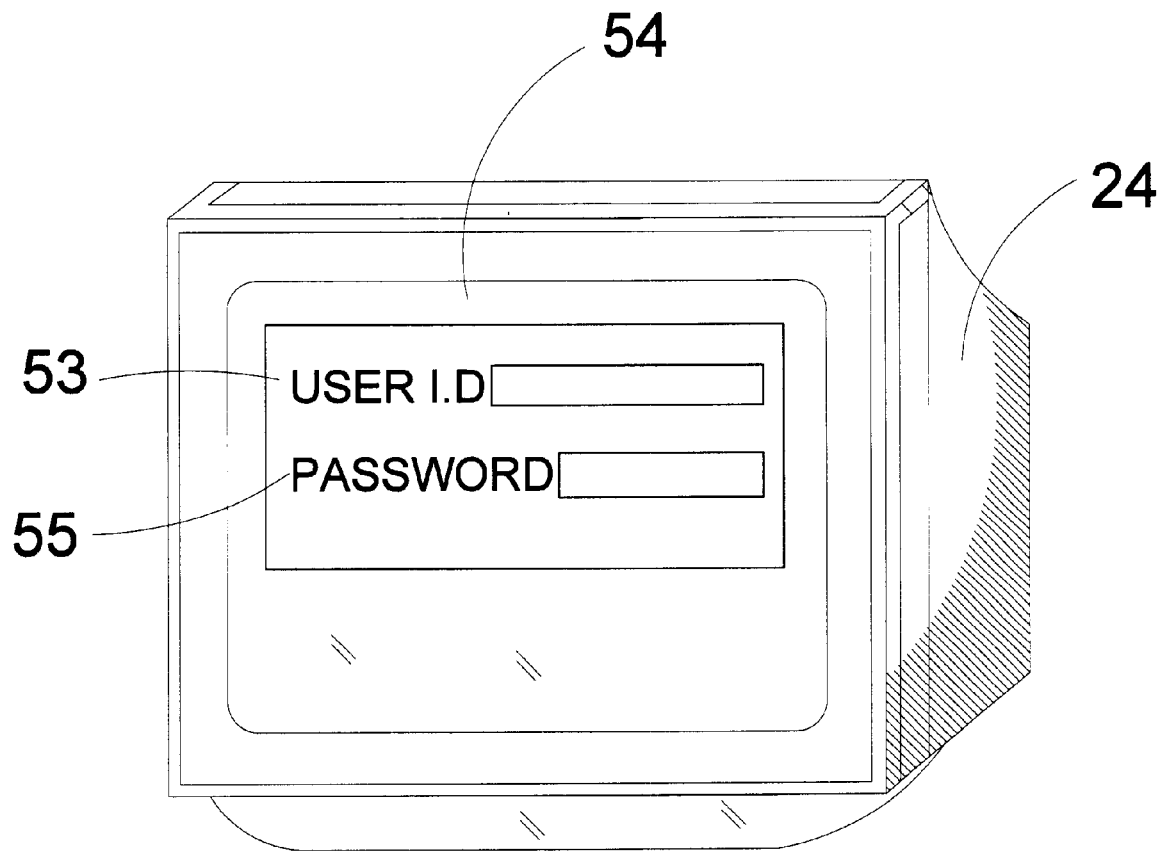
FIG. 5 is a front view of a computer monitor of the computer exercise system of the present invention showing a displayed prior to use of the computer indicating a password must be entered.

FIG. 5 illustrates the monitor 24 with a display 54 provided by the processor 16 prior to accessing the computer system 14 for use. This display 54 requests that the user input a user I.D. 53 and an associated password 55 using the keyboard 18. The input of the user I.D. 53 and associated password 55 activates the processor 16 to access the stored account information of the user. The account information stored in the memory 52 of the computer system 14 includes information regarding an exercise regimen for the user. This exercise regimen includes a predetermined time that the user must exercise prior to being granted access to use the computer system.

FIG. 6 illustrates an image 56 displayed subsequent to entry of the user I.D. 53 and associated password 55 and indicating a predetermined time period for which the user must exercise in order to be granted access to use the computer system 14. This image 56 is constantly updated by the processor 16 to indicate a time remaining for the user to exercise in order to be granted access to use the computer system 14. When the user begins to exercise, a signal is transmitted from the exercise machine 12 to the processor 16 indicating that the exercise machine 12 is being used. The processor 16 monitors this signal to determine that the exercise machine 12 is constantly being used during the predetermined time period and is connected to the timer 50 which measures the predetermined time period. As the time period is counted down by the timer 50, the processor 16 continually receives a signal from the timer 50 indicating the amount of time remaining for the user to exercise. Based upon this signal, the processor 16 continually updates the image 56 to indicate the time remaining for exercise. The processor 16 also continually monitors for receipt of the signal from the sensor 48 indicating the exercise device is in constant use. As long as the signal is received from the sensor 48, the processor 16 continues to update the time remaining for the user to continue exercising.

Upon the expiration of the time period, a subsequent image 58 as shown in FIG. 7 is displayed on the monitor 24 under the control of the processor 16. This image 58 indicates that the user has exercised for the predetermined time period and has been granted access to use the computer system 14.

The operation of the computer exercise system 10 will now be described with reference to the figures. In operation, the computer exercise system 10 is connected such that a sensor 48 is connected to the exercise device 12 so as to be able to sense use of the exercise device 12. The sensor 48 is connected to an input port of the processor 16 of the computer system 14 so as to transmit signals thereto when the sensor 48 senses use of the exercise device 12. Prior to use, an account including a user I.D. and password for all potential users must be loaded into the memory 52 of the processor 16. This is performed using the keyboard 18 of some other input device such as a scanning device or the disk drives by reading the information from a storage medium such as a floppy disk or a compact disk. For each account, a specific predetermined exercise time is also entered for the account. The computer exercise system 10 is now ready for use.

Prior to use, the monitor 24 will display an image thereon requesting input of a user I.D. and a password 55. When a user desires to use the computer system 14, the user will enter a user I.D. and password in the appropriate locations. Upon receipt of the user I.D. and password, the processor 16 accesses the account of the user and checks for a predetermined time period for exercise prior to granting access to the computer system 12. Upon determining the predetermined time period, the processor 16 controls the monitor to display an image indicating the predetermined time period as shown in FIG. 6. The processor 16 then monitors for receipt of a signal from the sensor 48 connected between the exercise device 12 and the processor 16. Upon receipt of the signal from the sensor 48, the processor 16 triggers the timer 50 to begin counting for the predetermined time period. As the processor 16 continues to receive signals from the sensor 48, the timer continues to count and the processor 16 continually updates the image on the monitor with an updated time period for the user to exercise. During the period of exercise, physical conditions of the user are also monitored. These conditions include but are not limited to heart rate, blood pressure and pulse rate. A signal representative of the measured physical conditions is transmitted to the processor 16 for storage and analysis of the physical condition of the user.

Should the processor 16 fail to receive a signal from the sensor 48 for a predetermined period prior to expiration of the predetermined time period, the processor will reset the timer 50 and prevent the user from gaining access t the computer system 14. If the processor 16 continues to receive a signal from the sensor 48 indicating the exercise device 12 is being used for a period equal to the predetermined time period, upon expiration of the time period, the processor 16 will grant access tot he computer system 14. The processor 16 will also control the monitor 24 to display an image 58 as seen in FIG. 7 indicating the user has completed the required exercise and has been granted access to the computer system 14. Upon expiration of the required exercise time period, the processor determines if a predetermined time period for using the computer has been set. If a predetermined time period for use has been set, the processor activates the timer to monitor this time period and inform the processor upon expiration of the time period. The user may now use the computer system 14 as desired. Once the user is granted access to the computer system, the user may perform all sorts of functions including but not limited to calculations, printing, charting, graphing, generating schedules, cross-referencing results of previous workouts. If a predetermined time period has been set, upon expiration of the time period, the processor notifies the user that it will shut down shortly and that all work should be completed. Otherwise, the user may use the computer for as long as desired. Should subsequent users desire to use the computer system or the same user log off and then wish to use the computer system again, the process must be repeated from log in by entering a user I.D. and password. The processor may also be set up to track the use of each user and not require a user to exercise more than a predetermined number of times within a particular time period for access to the computer system. For example, if a user has logged on to the computer system twice in one day and was required to exercise each time, should the user desire to use the computer system a third time, the processor 16 will grant access thereto without requiring the user to exercise another time.

From the above description it can be seen that the computer exercise system of the present invention is able to overcome the shortcomings of prior art devices by providing a computer exercise system which is able to insure that a user will exercise their body prior to operating a computer. The computer exercise system is provided with a user I.D. and password for each individual user of a computer, requiring each user to exercise for a predetermined amount of time after entering the user I.D. and password prior to operating the computer, preventing users from accessing software until a predetermined amount of exercise is performed. The computer exercise system includes an exercise device connected to an input port of a computer for transmitting a signal to a processor of the computer while exercise is being performed by a user and a scanner connected to the exercise device for determining when the exercise device is being operated. The computer exercise system also includes a timer connected to the processor for monitoring a time period during which exercise must be performed by the user. Furthermore, the computer exercise system of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed a new and desired to be protected by Letters Patent is set forth in the appended claims:

1. A computer exercise system for requiring a user to exercise prior to being granted access to use a computer, said computer exercise system comprising:
   a) a computer including a processor and a monitor;
   b) an exercise device;
   c) a sensor connected between said computer and exercise device for detecting use of said exercise device and, upon detecting of use of said exercise device, transmitting a signal to said processor indicating such use, wherein said processor prevents access to said computer until the signal is received from said sensor for a predetermined period of time;
   d) said monitor displaying an image indicating a period of time remaining in the use of said exercise device in order to be granted access to said computer while a user is using said exercise device;
   e) means comprising a keyboard for inputting to said processor a user I.D. and password, said processor having a memory in which is stored a time required for the user to spend operating said exercise machine in order to obtain access to said computer.

2. The computer exercise system as recited in claim 1, wherein said computer further includes a monitor connected to said processor for displaying an image indicating a period of time for which the signal must be received by said processor from said scanner in order to be granted access to said computer.

3. The computer exercise system as recited in claim 1, wherein said memory stores account information for a plurality of individual users, wherein each individual user is assigned an account and each account is assigned a unique user I.D. and password.

4. The computer exercise system as recited in claim 3, wherein each individual account includes a predetermined exercise time during which a respective user must exercise prior to being granted access to said computer.

5. The computer exercise system as recited in claim 1, wherein said sensor includes a transmitter and said computer further includes a receiver connected to said processor, said sensor wirelessly transmitting the signal indicating said exercise device is in use to said receiver for processing by said processor.

6. The computer exercise system as recited in claim 1, wherein said exercise device is a stationary bicycle.

7. The computer exercise system as recited in claim 1, wherein said exercise device is one of a stationary bicycle, a treadmill, a life cycle, a stair climbing machine or any cardiovascular device.

8. The computer exercise system as recited in claim 1, further comprising a connection cable connecting said sensor to said processor for transmitting the signal indicating said exercise device is in use from said sensor to said processor.

9. The computer exercise system as recited in claim 1, further comprising a physical conditioning monitor connected to said exercise device for monitoring a physical condition of the user while exercising.

10. The computer exercise system as recited in claim 1, wherein the user is able to perform functions including calculations, printing, charting, graphing, generating schedules, cross-referencing results of previous workouts upon being granted access to said computer.

11. A method of providing restricted access to a computer system, said method comprising the steps of:

a) connecting a sensor for detecting use to an exercise device;

b) accessing a computer by inputting a user I.D. and password;

c) said computer setting a predetermined exercise time for a user prior to granting access to the computer system and displaying said exercise time on a monitor;

d) detecting use of the exercise device by the sensor;

e) transmitting a signal indicative of the use of the exercise device by the sensor to the processor;

f) monitoring for receipt of the signal from the sensor by the computer during the predetermined time period and displaying on said monitor time remaining before access to the computer can be granted while a user is using said exercise device;

g) granting access to the computer system upon expiration of the predetermined time period upon determining by the processor that the signal has been received from the sensor throughout the predetermined time period;

h) storing in said computer multiple registered users' I.D.'s and passwords so that any registered user can obtain use of the computer after a preselected time of use of said exercise machine as stored in said computer; and i) said registered user accessing said computer for use of said computer for a time dependent on the amount of time the user exercised.

12. The method as recited in claim 11, wherein the signal is transmitted by the sensor to the computer through a cable wire.

13. The method as recited in claim 11, wherein the signal is wirelessly transmitted by the sensor to the computer.

14. The method as recited in claim 11, wherein the user I.D. and password are input using a keyboard connected to the computer.

15. The method as recited in claim 11, wherein the processor displays an amount of time remaining during the predetermined time period on a monitor.

16. The method as recited in claim 11, wherein the exercise device is a stationary bicycle and the sensor senses rotation of the wheel of the stationary bicycle to determine the stationary bicycle is in use.

17. The method as recited in claim 11, wherein a timer is connected to the processor and the timer is activated by the processor to count for the predetermined time period.

18. The method as recited in claim 11, wherein a processor in said computer prevents access to the computer system upon an interruption in receipt of the signal from the sensor during the predetermined time period.

19. The method of claim 11, further comprising the step of measuring a physical characteristic of user during exercising.

20. The method of claim 19, further comprising the step of transmitting a signal indicative of the measured physical characteristic to the computer for analysis of a physical condition of the user.

21. The method of claim 11, further comprising the step of setting a predetermined time period for use of the computer after completion of the predetermined exercise time.

* * * * *